United States Patent

Gross

(10) Patent No.: US 9,808,176 B2
(45) Date of Patent: Nov. 7, 2017

(54) METHOD AND MAGNETIC RESONANCE SYSTEM FOR MAGNETIC RESONANCE THERMOMETRY

(71) Applicant: Patrick Gross, Ismaning (DE)

(72) Inventor: Patrick Gross, Ismaning (DE)

(73) Assignee: Siemens Aktiengesellschaft, Munich (DE)

(*) Notice: Subject to any disclaimer, the term of this patent is extended or adjusted under 35 U.S.C. 154(b) by 813 days.

(21) Appl. No.: 14/220,427

(22) Filed: Mar. 20, 2014

(65) Prior Publication Data

US 2014/0285197 A1    Sep. 25, 2014

(30) Foreign Application Priority Data

Mar. 20, 2013   (DE) .................. 10 2013 204 880

(51) Int. Cl.
*G01R 33/48* (2006.01)
*A61B 5/055* (2006.01)
*A61B 5/01* (2006.01)

(52) U.S. Cl.
CPC .......... *A61B 5/055* (2013.01); *A61B 5/01* (2013.01); *G01R 33/48* (2013.01); *G01R 33/4804* (2013.01)

(58) Field of Classification Search
CPC ...... G01R 33/48; G01R 33/4804; A61B 5/01; A61B 5/055
See application file for complete search history.

(56) References Cited

U.S. PATENT DOCUMENTS

| 8,368,401 | B2* | 2/2013 | Levy | G01R 33/4804 |
| | | | | 324/315 |
| 9,289,154 | B2* | 3/2016 | Schmidt | G01R 33/4804 |
| 9,360,544 | B2* | 6/2016 | Huang | G01R 33/4804 |
| 9,541,621 | B2* | 1/2017 | Levy | G01R 33/4804 |

OTHER PUBLICATIONS

Salomir et al., "Reference-less PRFS MR thermometry using a thin open border and the harmonic functions theory: 2D experimental validation," ISMRM 2010, abstract No. 247 (2010).
Rieke et al., "MR Thermometry," J. Magn. Res. Imag., vol. 27, pp. 376-390 (2008).
McDannold et al., "Transcranial MRI-guided focused ultrasound surgery of brain tumors: Initial findings in three patients," Neurosurgery, vol. 66, No. 2, pp. 323-332 (2010).

* cited by examiner

*Primary Examiner* — Dixomara Vargas
(74) *Attorney, Agent, or Firm* — Schiff Hardin LLP

(57) ABSTRACT

In magnetic resonance (MR) thermometry, first and second magnetic resonance data that are acquired sequentially, from which a phase shift is determined between a measurement phase and a reference phase. In a first region of an examined person, the measurement phase is determined from the second magnetic resonance data and the reference phase is determined from the first magnetic resonance data. In a second region of the examined person, both the reference phase and measurement phase are determined from the second magnetic resonance data. Techniques for reference-based magnetic resonance thermometry and reference-free magnetic resonance thermometry can be applied.

9 Claims, 4 Drawing Sheets

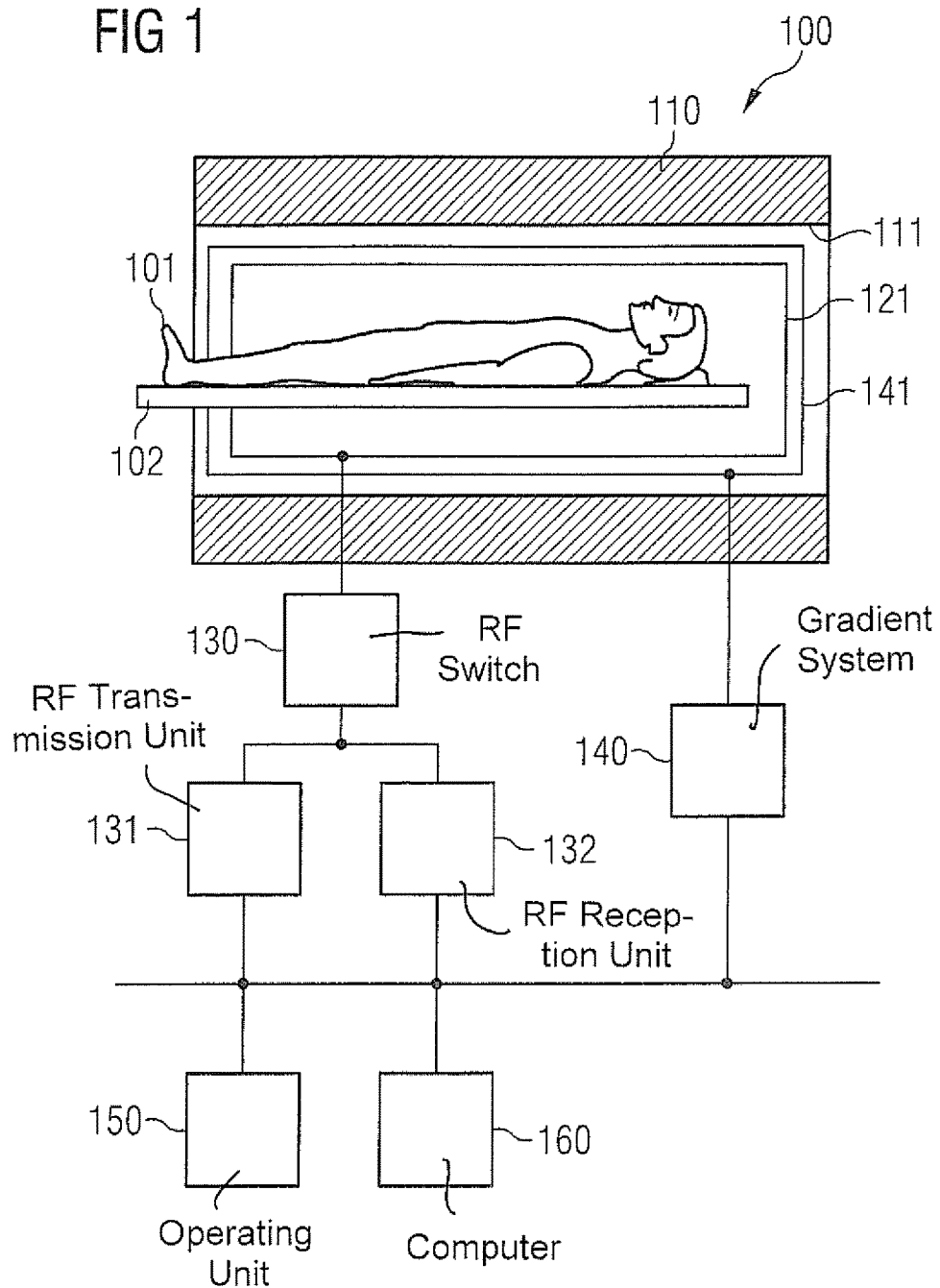

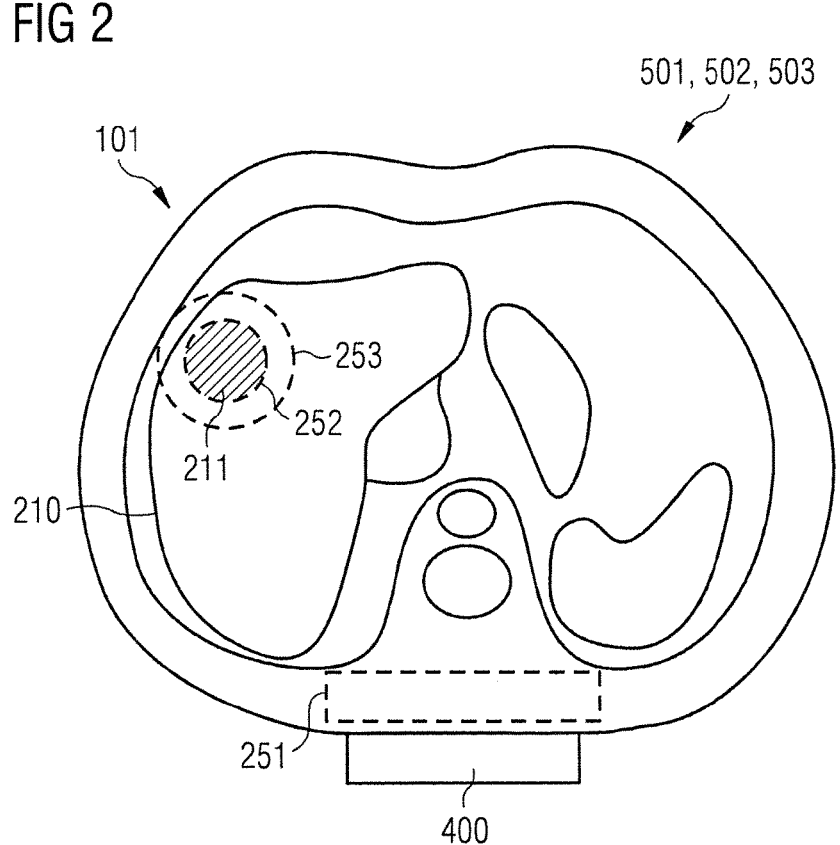

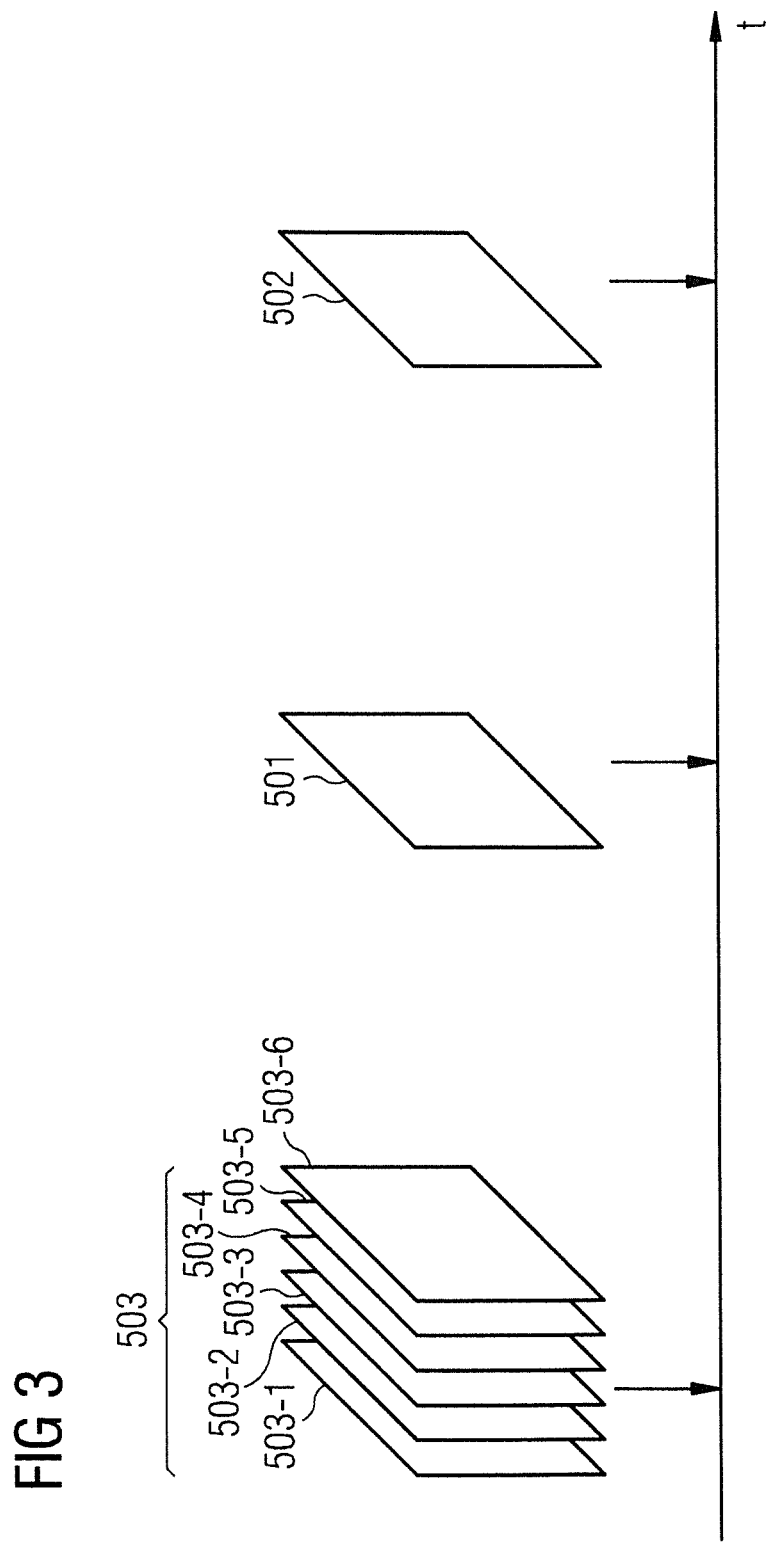

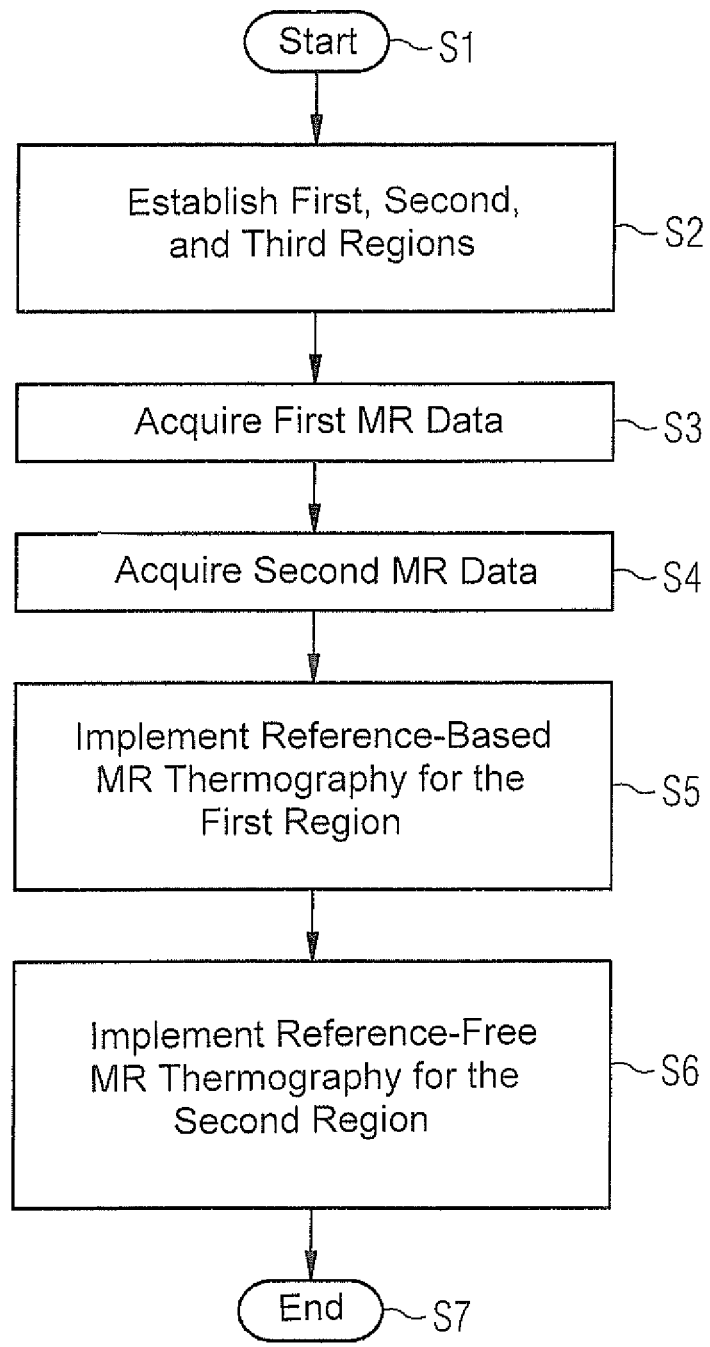

METHOD AND MAGNETIC RESONANCE SYSTEM FOR MAGNETIC RESONANCE THERMOMETRY

BACKGROUND OF THE INVENTION

Field of the Invention

The present invention concerns techniques for magnetic resonance thermometry and a magnetic resonance system for implementing such techniques. In particular, the invention concerns techniques for thermometry based on phase shifts in acquired MR data that take into account different reference phases for different regions of an examined person.

Description of the Prior Art

In magnetic resonance (MR) imaging, structures and/or parameters of an examined person are imaged. For this purpose, a magnetization of protons is deflected out of the steady state (typically parallel to a basic magnetic field) by radiation of a radio-frequency (RF) pulse. The excited transverse magnetization oscillates and can be measured by means of inductive measurement techniques. The MR data acquired in such a manner depict the structures and/or properties.

It is possible to implement MR imaging such that the contrast in the MR data or in MR images is indicative of a temperature (MR thermometry). For example, MR thermometry is based on the physical effect that the proton resonance frequency (PRF) shows a dependency on the temperature. Typically this is a linear dependency. Therefore, a transverse magnetization excited within the scope of MR thermometry shows a corresponding dependency of the acquired phase on the temperature. Phase shifts are typically measured between a measurement phase and a reference phase; for example, see in this regard Equation 16 from "MR Thermometry" by V. Rieke and K. B. Pauly in J. Mag. Reson. Med. Imag. 27 (2008) 376-390.

Techniques are known that obtain the reference phase from reference MR data that represent an image an examined person, for example at a known reference temperature before the introduction of heat (reference-based MR thermometry). In other words, a "historic" reference MR image is used to determine the temperature. For example, see the aforementioned publication by V. Rieke.

Techniques are also known that obtain the reference phase from the same MR data from which the measurement phase is also obtained, but from a different imaged region, for example (reference-free MR thermometry). See for example R. Salomir et al., Proc. Intl. Soc. Mag. Reson. Med. 18 (2010) 247.

Different applications or imaged regions respectively have advantages and disadvantages relative to these aforementioned techniques of MR thermometry. It is frequently not possible, or only possible to a limited extent, to image different items equally well with both techniques.

In particular, periodic movements, for example translation, rotation, expansion, compression, etc., of organs and body regions on a characteristic time scale of seconds to minutes (inter-fraction motion) can hinder the application of reference-based MR thermometry. This is the case since a significant movement can already have occurred between the acquisition of the MR data which are used to determine the reference phase and the acquisition of the MR data which are used to determine the measurement phase, and there is thereby no or only a slight phase coherence between the two MR data.

The use of reference-free thermometry can be possible only to a limited extent if the phase coherence is spatially limited, meaning that a variation of the phase over the location occurs due to susceptibility fluctuations, for example.

A need therefore exists for improved techniques of MR thermometry which enable a particularly precise measurement of the temperature.

SUMMARY OF THE INVENTION

The invention concerns a method for MR thermometry of an examined person using techniques that determine a temperature-indicative phase shift between a measurement phase and a reference phase in MR data. The method includes the acquisition of first MR data for the examined person at a first point in time and the acquisition of second MR data for the examined person at a second point in time that occurs after the first point in time. Furthermore, the method includes the determination of a temperature in a first region of the MR data by determining the phase shift between a) the second MR data in the first region as a measurement phase and b) the first MR data in the first region as a reference phase. Furthermore, the method includes the determination of a temperature in a second region of the MR data by determining the phase shift between a) the second MR data in the second region as a measurement phase and b) the second MR data in a third region that is arranged adjacent to the second region as a reference phase.

The determination of the temperature in the first region can thus take place by means of reference-based thermometry techniques, and the determination of the temperature in the second region can take place by means of reference-free thermometry techniques.

For example, the method can furthermore include: receive a signal which is indicative of an introduction of heat into the examined person, for example in particular at the second region. For example, introduction of heat can occur within the scope of minimally invasive thermal therapy methods. A prevalent technique is the use of focused ultrasound (FUS) and high-intensity focused ultrasound (HIFU). For example, the signals can be obtained during the acquisition of the second MR data; no signals can be obtained during the acquisition of the first data. In other words: an introduction of heat into the examined person can only occur after the first point in time.

Therefore, it can also be possible for the first MR data to constitute an image the examined person with a known reference temperature. The reference phase therefore can be indicative of a reference temperature relative to which a temperature shift is determined.

For example, "adjacent" can mean that the third region is immediately adjoining or slightly distant relative to the second region. The third region can entirely or partially surround the second region. For example, "adjacent" can mean that a shortest distance between the second region and third region is small relative to a length scale of a susceptibility variation within the examined person at which a phase incoherency can occur. For example, "adjacent" can mean: distance less than 30 cm, advantageously less than 10 cm, particularly advantageously less than 3 cm.

An improved temperature determination can be enabled by the use of a different data foundation as a reference phase for the first and second region. Namely, it can be enabled that a particularly suitable MR thermometry technique is respectively applied in the different regions of the examined person. The temperature can be determined more precisely.

For example, the first region can include anatomical regions that exhibit no significant intra-fraction motion. The second region can include anatomical regions that exhibit significant intra-fraction motion.

Intra-fraction motions can be distinguished from inter-fraction motions that occur on a longer characteristic time scale (for example hours or days). The cause of intra-fraction motion can in particular be breathing and/or heart-beat of the examined person, i.e. on time scales of seconds to minutes. The intra-fraction motion can in particular occur cyclically or, respectively, periodically.

This time scale can be somewhat comparable to the time scale at which the first and second MR data are acquired, meaning that the time scale is on the order of a time difference between the first and second points in time. Therefore, intra-fraction motion can already produce a significant phase drift between identical regions in the first and second MR data. Therefore, a comparably precise temperature determination in the second region can be possible by means of reference-free MR thermometry.

The first and second regions can respectively represent a relevant measurement region (region of interest). For example, the first and second regions comprise relevant anatomical structures. For example, the first and second region respectively include regions to be monitored given parallel FUS or HIFU applications that can be indexed via the obtained signals. For example, the first region can include a near region or, respectively, a near field of the radiated ultrasound waves, while the second region can include, for example, a target region of the radiated ultrasound waves, for example in which a particularly strong temperature increase is sought.

The method can include establishment of the first region, the second region and the third region using a series of additional MR data that are acquired before the first and second points in time.

Furthermore, the method can include the acquisition of a series of MR data. The series of additional MR data can include one or more MR data. For example, the establishment can be performed manually by an operator, or semi-automatically or fully automatically by landmark detection and segmentation of anatomically relevant features.

For example, the series of MR data can image a time dependency of a motion of the examined person, for example due to intra-fraction motion. In such a case, for example, it would be possible to identify different motion phases of a cyclical intra-fraction motion. For the different motion phases it would then be possible to determine different reference phases from multiple first MR data. In combination with gating and/or trigger techniques, a particularly precise determination of the temperature can then be possible. It is possible that the acquisition of the first MR data and/or the second MR data is implemented based on a breath triggering of a breathing of the examined person.

The method can furthermore include a spatially resolved determination of a first temperature curve for the series of additional MR data that is implemented by determining a phase shift between a) every respective additional MR data of the series of additional MR data as a measurement phase and b) defined additional MR data as a reference phase. The method can also include a spatially resolved determination of a second temperature curve for the series of additional MR data that is implemented by determining a phase shift between a) a corresponding region in each additional MR data set as a measurement phase and b) a region adjacent to the corresponding region in the same respective additional MR data as a reference phase. Furthermore, the method can include: spatially resolved evaluation of the first temperature curve and the second temperature curve, wherein the establishment of the first region and the second region and the third region is based on the evaluation of the first and second temperature curve.

For example, the defined additional MR data can be the first acquired MR data of the series of MR data. In other words, the reference phase of the first temperature curve can then respectively be related to the same (for example first acquired) data foundation; the reference phase of the second temperature curve can accordingly respectively originate from the MR data from which the measurement phase is also determined. The first temperature curve can be determined from the series of additional MR data by reference-based MR thermometry, while the second temperature curve can be determined by means of reference-free MR thermometry.

It can thus be tested as to which regions reference-free thermometry is particularly well suited, and for what regions reference-based thermometry is particularly well suited. The establishment of the regions can then take place particularly precisely so that the subsequent temperature determination is particularly precise.

It is possible for no introduction of heat into the examined person to take place during the acquisition of the series of additional MR data. The first region can comprise those regions in which the first temperature curve is temperature-stable. The second region can comprise those regions in which the second temperature curve is temperature-stable.

If no controlled temperature introduction into the examined person takes place during the acquisition of the series of MR data, it can be possible that the temperature remains essentially constant during the acquisition of the MR data. A temperature fluctuation measured in the first or second temperature curve can then be indicative of phase drift that does not originate in an actual varied temperature. For example, such phase drifts due to measurement technology can occur due to intra-fraction motion or due to spatial phase incoherency. In other words: a measured temperature dependency in the first (second) temperature curve can be indicative of a reduced confidence of the reference-based (reference-free) MR thermometry.

The invention also concerns an MR system that includes a receiver unit and a computer. The receiver unit is designed in order to implement the following steps: acquire first MR data for the examined person at a first point in time; and acquire second MR data for the examined person at a second point in time that is after the first point in time. The computer is configured in order to implement the following steps: determine a temperature in a first region of the MR data by determining the phase shift between a) the second MR data in the first region as a measurement phase and b) the first MR data in the first region as a reference phase; and determine a temperature in a second region of the MR data by determining the phase shift between a) the second MR data in the second region as a measurement phase and b) the second MR data in a third region that is arranged adjacent to the second region as a reference phase.

The MR system can be configured in order to implement a method for MR thermometry according to a further aspect of the invention.

For such an MR system, effects can be achieved that are comparable to effects that can be achieved for a method for MR thermometry according to a further aspect of the invention.

The features described above and features that are described in the following can be used not only in the corresponding, explicitly presented combination, but also in additional combinations or in isolation, without departing from the scope of the present invention.

BRIEF DESCRIPTION OF THE DRAWINGS

FIG. 1 schematically illustrates an MR system operable in accordance with the invention.

FIG. 2 is a section view of an examined person, in which a first region and a second region for MR thermometry are illustrated according to various embodiments.

FIG. 3 illustrates a chronological sequence of the acquisition of MR data.

FIG. 4 is a flow chart of a method for MR thermometry according to various embodiments of the invention.

DESCRIPTION OF THE PREFERRED EMBODIMENTS

In the following, the present invention is explained in detail using preferred embodiments with reference to the figures. Identical reference characters in the figures denote identical or similar elements.

In FIG. 1, an MR system 100 is shown that is desired to implement corresponding techniques, methods and steps according to the invention. The MR system 100 has a magnet 110 that defines a tube 111. The magnet 110 generates a basic magnetic field parallel to its longitudinal axis. An examination subject (here an examined person 101) on a bed table 102 can be slid into the magnet 110. The MR system 100 furthermore has a gradient system 140 to generate gradient fields that are used for MR imaging and for spatial coding of acquired raw data. The gradient system 140 typically comprises at least three gradient coils 141 that can be controlled separately and positioned in a well-defined manner relative to one another. The gradient coils 141 enable gradient fields to be applied and switched along defined spatial directions (gradient axes). The gradient fields can be used for slice selection, for frequency coding (in the readout direction) and for phase coding, for example. A spatial coding of the raw data thus can be achieved.

An RF coil arrangement 121 that can radiate an amplitude-modulated RF excitation pulse into the examined person 101 is provided for excitation of the polarization resulting in the basic magnetic field or alignment of the magnetization in the longitudinal direction. A transverse magnetization can thereby be generated. To generate such RF excitation pulses, an RF transmission unit 131 is connected via an RF switch 130 with the RF coil arrangement 121. The RF transmission unit 131 can include an RF generator and an RF amplitude modulation unit.

Furthermore, an RF reception unit 132 is coupled via the RF switch 130 with the RF coil arrangement 121. MR signals of the relaxing transversal magnetization can be acquired via the RF reception unit 132 as raw data, for example via inductive injection into the RF coil arrangement 121.

The MR system 100 furthermore has an operating unit 150 which, for example, can comprise a monitor, a keyboard, a mouse etc. User inputs can be detected and output to the user can be realized by means of the operating unit 150. For example, it can be possible for individual operating modes or operating parameters of the MR system to be set by the user and/or automatically and/or via remote control by means of the operating unit 150.

Furthermore, the MR system 100 has a computer 160. For example, the computer 160 can be set up in order to administer various tasks. For example control a measurement sequence for data acquisition, evaluation acquired MR data (for MR thermometry, for example) etc.

A side view of the examined person 101 is shown in FIG. 2. For example, the side view can be imaged by MR data 501, 502, 503. In contrast to FIG. 1, the examined person 101 is in the prone position in FIG. 2. A HIFU transceiver 400 enables introduction of heat into the examined person 101 for thermal therapy of a target region 211 (shown shaded in FIG. 2). The target region 211 is located in the liver 210 of the examined person 210. Additional organs and anatomical regions are shown in FIG. 2.

A first region 251 has a near field of the HIFU transceiver 400. It can be worthwhile to determine a temperature in the first region 251 in order to monitor the near field of the HIFU transceiver 400. A second region 252 comprises the target region 211. It can be worthwhile to determine a temperature in the second region 252 in order to monitor the target region 211, for example while ultrasound is being used for thermal ablation.

The computer 160 is configured to implement a reference-based MR thermometry in the first region 251 and to implement a reference-free MR thermography in the second region 252.

An intra-fraction motion can typically be significant in the region of the liver 210, and therefore in the second region 252, while no (or only a slight) intra-fraction motion is present in the first region 251. In order to avoid phase drifts relative to the reference MR data, reference-free MR thermometry is therefore applied in the second region 252. In reference-free thermometry, the reference phase is obtained from the same MR data from which the measurement phase is obtained, but from a third region 253 that surrounds and adjoins the second region in the scenario of FIG. 2. Because no significant susceptibility variations exist between the second and third region 252, 253, the magnetization phase is stable or, respectively, phase-coherent. Therefore, the MR data from the third region 253 are particularly suitable as a reference phase for the measurement phase from the second region 252.

Because the first region 251 is situated particularly close to the skin surface of the examined person 101, here it can be impossible (or possible only to a limited extent) to apply reference-free thermography. This is the case because strong susceptibility fluctuations are present in proximity to the first region 251, and therefore the magnetization phase over the location is comparably unstable or incoherent.

The establishment of the regions 251, 252, 253 can be implemented semi-automatically or manually, for example. For example, the regions 251, 252, 253 can be identified in additional MR data 503 that are acquired before the actual temperature measurement. Techniques of segmentation and/or landmark detection can be used for semi-automatic and fully automatic scenarios.

The MR data 503 may include a series of MR images. If the series of additional MR data 503 is acquired without temperature introduction (i.e. with the HIFU transceiver 400 deactivated), it can be assumed that the temperature is approximately constant across the series of additional MR data 503. The series of additional MR data 503 can then be evaluated by means of reference-based and reference-free MR thermometry. The temperature curves obtained in such a manner show no or only a slight (strong) time dependency on the temperature, such that this can be an indicator that the corresponding regions are suitable (unsuitable) for the respective technique. Corresponding considerations can be taken into account in the establishment of the regions 251, 252, 253.

It would also be possible that both the first temperature curve and second temperature curve indicate temporally fluctuating temperature. For such regions, MR thermometry can then be precluded since here both reference-free and reference-based MR thermometry are only functional to a limited extent.

It can also be possible to identify periodicities in the motion using the series of additional MR data 503, and to use gating or trigger techniques based on these.

A chronological sequence of the acquisition of MR data 501, 502, 503 is illustrated in FIG. 3. First, the series of additional MR data 503 is acquired, which series comprises six additional MR data 503-1-503-6 in the example of FIG. 3.

For example, each of the additional MR data 503-1-503-6 can respectively be used with spatial resolution for reference-based MR thermometry, for example, with regard to the additional MR data 503-1 from which the reference phase can be obtained.

It is also possible to determine a temperature curve for the additional MR data 503-1-503-6 by means of spatially resolved, reference-free MR thermometry. For this, the measurement phase and reference phase can respectively be determined from the same additional MR data 503-1-503-6 for different pixels or regions. The acquisition of the first MR data 501 subsequently takes place at a first point in time, and the second MR data 502 are acquired at a second point in time. An introduction of heat—for example via operation of the HIFU transceiver 400—can take place after the acquisition of the first MR data 501.

A flow chart of a method for MR thermometry according to various embodiments is presented in FIG. 4. The method begins in Step S1. The establishment of the first region 251, the second region 252 and the third region 253 then takes place in Step S2, for example using the additional MR data 503. The establishment can be implemented under consideration of temperature curves obtained by means of reference-based and reference-free MR thermometry.

The acquisition of the first MR data 501 and the second MR data 502 takes place in Steps S3 and S4.

In Step S5, the reference-based MR thermometry for the first region 251 is implemented based on the first and second MR data 501, 502.

In Step S6, the reference-free MR thermometry for the second region 252 is implemented based on the second MR data 502.

The method ends in Step S7.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for magnetic resonance (MR) thermometry of a patient, comprising:
    operating an MR data acquisition unit, in which the patient is situated, to acquire first MR data from the patient at a first point in time;
    operating said MR data acquisition unit in which said patient is situated to acquire second MR data from the patient at a second point in time that occurs after said first point in time;
    providing said first MR data and said second MR data to a computerized processor and, in said processor, automatically determining a temperature of a first region of the patient by determining a phase shift between said second MR data in said first region, as a measurement phase, and said first MR data in said first region, as a reference phase;
    in said processor, automatically determining a temperature in a second region of the patient, which is different from said first region, by determining a phase shift between said second MR data in said second region, as a measurement phase, and said second MR data in a third region of the patient that is different from said first region, and that is situated adjacent to said second region, as a reference phase; and
    making the temperature determined in at least one of said first region or said second region available at an output of said processor in electronic form.

2. A method as claimed in claim 1 comprising operating said MR data acquisition unit with said patient situated therein, prior to said first point in time, to acquire a plurality of sets of additional MR data from the patient; and
    providing said sets of additional MR data to said processor and, in said processor, establishing said first region and said second region and said third region from said sets of additional MR data.

3. A method as claimed in claim 2 comprising, in said processor:
    determining a spatially resolved first temperature curve for said sets of additional MR data by determining a phase shift between each individual set of additional MR data, as a measurement phase, and defined data among said additional MR data, as a reference phase;
    determining a spatially resolved second temperature curve for said sets of additional MR data by determining a phase shift between a same region in each individual additional MR data set, as a measurement phase, and a region adjacent to said same region in each individual set of additional MR data, as a reference phase; and
    establishing said first region and said second region and said third region dependent on a spatially resolved evaluation of said first temperature curve and said second temperature curve.

4. A method as claimed in claim 3 comprising:
    allowing no introduction of heat into said patient during acquisition of said sets of additional MR data; and
    determining said first region as at least one region of the patient for which said first temperature curve is temperature-stable; and
    determining said second region as at least one region of the patient for which said second temperature curve is temperature-stable.

5. A method as claimed in claim 2 comprising establishing said first and second regions in said processor by:
    segmenting said sets of additional MR data to segment selected anatomical regions therein, as segmented regions; and
    establishing said first region and said second region and said third region for said segmented regions.

6. A method as claimed in claim 1 comprising, in said processor:
    establishing said first region as at least one anatomical region of the patient that exhibits no significant intra-fraction motion; and
    establishing said second region as a region of the patient comprising at least one anatomical region that exhibits significant intra-fraction motion.

7. A method as claimed in claim 1 comprising, in said processor:
   determining said temperature in said first region using a reference-based thermometry technique; and
   determining said temperature in said second region using a reference-free thermometry technique.

8. A method as claimed in claim 1 comprising:
   acquiring a respiratory signal from the patient situated in the MR data acquisition unit; and
   acquiring at least one of said first MR data and said second MR data dependent on a breathing trigger identified in said respiratory signal.

9. A magnetic resonance (MR) apparatus comprising:
   an MR data acquisition unit configured to receive a patient therein;
   a control unit configured to operate the MR data acquisition unit, while the patient is situated therein, to acquire first MR data from the patient at a first point in time;
   said control unit being configured to operate said MR data acquisition unit, while said patient is situated therein, to acquire second MR data from the patient at a second point in time that occurs after said first point in time;
   a computerized processor provided with said first MR data and said second MR data, said processor being configured to automatically determine a temperature of a first region of the patient by determining a phase shift between said second MR data in said first region, as a measurement phase, and said first MR data in said first region, as a reference phase;
   said processor being configured to automatically determine a temperature in a second region of the patient, which is different from said first region, by determining a phase shift between said second MR data in said second region, as a measurement phase, and said second MR data in a third region of the patient that is different from said first region, and that is situated adjacent to said second region, as a reference phase; and
   said processor being configured to make the temperature determined in at least one of said first region or said second region available at an output of said processor in electronic form.

* * * * *